(12) United States Patent
Rothstein (10) Patent No.: US 9,364,637 B2
(45) Date of Patent: Jun. 14, 2016

(54) TRANSCATHETER BALLOON-ASSISTED MITRAL VALVE NAVIGATION DEVICE AND METHOD

(75) Inventor: Paul Rothstein, Elk River, MN (US)

(73) Assignee: Medtronic, Inc., Minneapolis, MN (US)

( * ) Notice: Subject to any disclaimer, the term of this patent is extended or adjusted under 35 U.S.C. 154(b) by 489 days.

(21) Appl. No.: 13/225,735

(22) Filed: Sep. 6, 2011

(65) Prior Publication Data

US 2013/0060328 A1 Mar. 7, 2013

(51) Int. Cl.
| | |
|---|---|
| *A61F 11/00* | (2006.01) |
| *A61M 25/04* | (2006.01) |
| *A61M 25/10* | (2013.01) |
| *A61F 2/24* | (2006.01) |
| *A61B 17/00* | (2006.01) |
| *A61M 25/09* | (2006.01) |

(52) U.S. Cl.
CPC ........... *A61M 25/04* (2013.01); *A61M 25/1002* (2013.01); *A61B 2017/00783* (2013.01); *A61F 2/2427* (2013.01); *A61M 2025/09125* (2013.01); *A61M 2025/1047* (2013.01)

(58) Field of Classification Search
CPC . A61F 2/2427; A61M 25/04; A61M 25/1002; A61M 25/065
USPC ................................. 623/1.11, 2.11; 606/108
See application file for complete search history.

(56) References Cited

U.S. PATENT DOCUMENTS

| | | | |
|---|---|---|---|
| 5,246,421 A * | 9/1993 | Saab ............................. 606/194 |
| 5,346,504 A * | 9/1994 | Ortiz et al. .................... 606/192 |
| 5,868,778 A | 2/1999 | Gershony et al. |
| 6,068,638 A * | 5/2000 | Makower ...................... 606/159 |
| 6,387,119 B2 * | 5/2002 | Wolf et al. .................... 606/108 |
| 6,547,767 B1 * | 4/2003 | Moein ........................... 604/264 |
| 6,595,989 B1 | 7/2003 | Schaer |
| 7,191,015 B2 | 3/2007 | Lamson et al. |
| 7,381,219 B2 | 6/2008 | Salahieh et al. |
| 7,731,681 B2 | 6/2010 | Schaer et al. |
| 7,785,366 B2 | 8/2010 | Maurer |
| 7,881,807 B2 | 2/2011 | Schaer |
| 2001/0034547 A1 * | 10/2001 | Hall et al. ..................... 623/1.11 |
| 2002/0026217 A1 * | 2/2002 | Baker et al. ................... 606/223 |
| 2002/0032476 A1 * | 3/2002 | Gambale et al. ................ 623/1.1 |
| 2004/0015193 A1 * | 1/2004 | Lamson et al. .................. 607/9 |
| 2004/0215229 A1 * | 10/2004 | Coyle ........................... 606/200 |
| 2005/0004647 A1 * | 1/2005 | Bassoe .......................... 623/1.11 |
| 2005/0021048 A1 * | 1/2005 | Kuhlman ............. A61M 25/065 606/108 |
| 2005/0216039 A1 * | 9/2005 | Lederman ...................... 606/144 |
| 2005/0283179 A1 * | 12/2005 | Lentz ............................ 606/192 |
| 2007/0112422 A1 * | 5/2007 | Dehdashtian ................ 623/2.11 |

(Continued)

FOREIGN PATENT DOCUMENTS

WO WO2009/061848 5/2009

*Primary Examiner* — Richard Louis (57) ABSTRACT

A method for positioning a centering introducer in a heart of a patient, which includes the steps of inserting an anchoring wire delivery catheter through a heart wall and to a treatment region of the heart, deploying at least one anchoring wire from the delivery catheter and into tissue in the treatment region of the heart, and removing the delivery catheter from the heart. A centering introducer can then be advanced along the anchoring wire to the treatment region, wherein the centering introducer includes an introducer element and at least one balloon. At least one of the balloons can then be inflated to reorient the introducer element in at least one direction relative to a longitudinal axis of the centering introducer.

19 Claims, 13 Drawing Sheets

(56) References Cited

U.S. PATENT DOCUMENTS

| | | | |
|---|---|---|---|
| 2007/0112425 A1* | 5/2007 | Schaller et al. | 623/2.37 |
| 2007/0219627 A1* | 9/2007 | Chu | A61B 17/0401 623/1.36 |
| 2008/0045863 A1 | 2/2008 | Bakos | |
| 2008/0114294 A1* | 5/2008 | Holman et al. | 604/96.01 |
| 2008/0234813 A1* | 9/2008 | Heuser | 623/2.11 |
| 2009/0287291 A1* | 11/2009 | Becking et al. | 623/1.11 |
| 2009/0306685 A1 | 12/2009 | Fill | |
| 2010/0030317 A1* | 2/2010 | Grabowski | A61F 2/856 623/1.11 |
| 2010/0076402 A1* | 3/2010 | Mazzone et al. | 604/509 |
| 2010/0298922 A1* | 11/2010 | Thornton et al. | 623/1.11 |

\* cited by examiner

Fig. 17

TRANSCATHETER BALLOON-ASSISTED MITRAL VALVE NAVIGATION DEVICE AND METHOD

TECHNICAL FIELD

The present invention relates generally to devices and methods for repair or replacement of heart valves, and more particularly to delivery systems and methods for accurately navigating to the area of the native mitral valve, such as for repairing the mitral valve area or for replacing a native mitral valve with a prosthetic heart valve.

BACKGROUND

One of the two atrio-ventricular valves in the heart is the mitral valve, which is located on the left side of the heart and which forms or defines a valve annulus and valve leaflets. The mitral valve is located between the left atrium and the left ventricle, and serves to direct oxygenated blood from the lungs through the left side of the heart and into the aorta for distribution to the body. As with other valves of the heart, the mitral valve is a passive structure in that it does not itself expend any energy and does not perform any active contractile function.

The mitral valve includes two moveable leaflets that open and close in response to differential pressures on either side of the valve. Ideally, the leaflets move apart from each other when the valve is in an open position, and meet or "coapt" when the valve is in a closed position. However, problems can develop with these valves, which can generally be classified as either stenosis, in which a valve does not open properly, or insufficiency (also called regurgitation), in which a valve does not close properly. Stenosis and insufficiency may occur independently or concomitantly in the same valve. The effects of valvular dysfunction vary, with mitral regurgitation or backflow typically having relatively severe physiological consequences to the patient. Regurgitation, along with other abnormalities of the mitral valve, can increase the workload placed on the heart. The severity of this increased stress on the heart and the patient, along with the ability of the heart to adapt to the increased stress, determine the treatment options that are available for a particular patient. In some cases, medication can be sufficient to treat the patient, which is the preferred option when it is viable; however, in many cases, defective valves have to be repaired or completely replaced in order for the heart to function normally.

One situation in which repair of a mitral valve can be viable is when the defects present in the valve are associated with dilation of the valve annulus, which not only prevents competence of the valve but also results in distortion of the normal shape of the valve orifice. Remodeling of the annulus is central to these types of reconstructive procedures to the mitral valve. When a mitral valve is repaired in this way, one common result is a reduction in the size of the posterior segment of the mitral valve annulus. As a part of the mitral valve repair, the involved segment of the annulus is diminished (i.e., constricted) so that the leaflets may coapt correctly on closing, and/or the annulus is stabilized to prevent post-operative dilatation from occurring. Either result is frequently achieved by the implantation of a prosthetic ring or band in the supra annular position. The purpose of the ring or band is to restrict, remodel and/or support the annulus to correct and/or prevent valvular insufficiency. Such repairs of the valve, when technically possible, can produce relatively good long-term results.

However, repair of the mitral valve area is sometimes either impossible or undesirable or has failed, such as in cases where dilation of the valve annulus is not the problem, leaving valve replacement as the preferred option for improving operation of the heart. In cases where the mitral valve is replaced, it can generally be replaced with either mechanical valves or bio-prosthetic or tissue valves. The surgical procedure for implantation of many of these mechanical and tissue valves involves opening the patient's chest to access the mitral valve through the left atrium, and sewing the new valve in position. In order to simplify surgical procedures and reduce patient trauma, methods and devices have recently been developed for replacing the mitral valve using minimally invasive and/or percutaneous replacement techniques and devices. In one exemplary valve replacement procedure, a replacement valve can be delivered in a compressed condition to the native valve site, where it is expanded for implantation into the target site in a patient. With specific regard the replacement of the mitral valve, a replacement mitral valve can be inserted into a balloon catheter and delivered percutaneously via the vascular system to the annulus of the native mitral valve, where the replacement valve can be expanded by a balloon.

Due to the relatively complicated path through which a delivery system must travel to reach the area of the mitral valve for either its repair or replacement, many delivery systems that are currently available cannot provide for consistent navigation to the desired area. Thus, there is a continued desire to provide for improved mitral valve delivery systems and repair or replacement procedures that accommodate the physical structure of the heart without causing undue stress to the patient during the operation on the heart.

SUMMARY

In one aspect of this invention, a delivery system and method are provided for guiding an introducer tip, introducer element, and/or other components to desired locations in the area of the mitral valve, such as the annular region of the mitral valve. In one embodiment, the method is used to navigate a catheter to areas of the heart that are typically difficult to reach, such as areas that are only reachable via a path that includes one or more curves that have a tight radius. Such delivery systems and methods may be desirable for a number of reasons, such as to insert anchors for a mitral annulus reduction, to orient a replacement mitral valve in the area of the native mitral valve annulus, to insert a clip or other device during a mitral valve repair procedure, for example.

One exemplary delivery system of the invention includes two separate catheters. One of these catheters includes an anchoring wire and its delivery system, while the other of the catheters is used as a centering introducer. With this delivery system, a guidewire and at least one anchoring wire are delivered to a desired area of the heart with an anchoring wire delivery system, and then this delivery system and guidewire are removed from the patient, while the anchoring wire is attached to tissue of the patient and therefore remains in the patient. The anchoring wire is then used in a similar manner as a guidewire for engagement with a lumen of a centering introducer (i.e., to facilitate a desired positioning of the centering introducer relative to the heart of a patient).

In accordance with an embodiment of the invention, a method is provided for positioning a centering introducer in a heart of a patient. The method includes the steps of inserting an anchoring wire delivery catheter through a heart wall and to a treatment region of the heart, deploying at least one anchoring wire from the delivery catheter and into tissue in the treatment region of the heart, and removing the delivery catheter from the heart. A centering introducer can then be advanced along an anchoring wire to the treatment region, wherein the centering introducer comprises an introducer element and at least one balloon. At least one of the balloons can then be inflated to reorient the introducer element in at least one direction relative to a longitudinal axis of the centering introducer. The method may further include inserting a guidewire through the heart wall and to the treatment region of the heart, and then advancing the anchoring wire delivery catheter along the guidewire. According to one aspect of the invention, the treatment region of the heart is the annular region of a mitral valve. Once the centering introducer and its introducer element are positioned in a desired location a treatment device, such as a clip, an anchor, or a replacement heart valve can be introduced through the introducer lumen and introducer element and into the treatment region of the heart.

In accordance with an embodiment of the invention, a delivery system is provided for positioning an introducer element relative to a predetermined area of the heart. The delivery system includes an anchoring wire delivery catheter comprising a guidewire lumen and an anchoring wire lumen, an anchoring wire that is slideably engageable within the anchoring wire lumen, and a centering introducer comprising an introducer element and at least one balloon. The centering introducer can further include an anchoring wire lumen that is slideably engageable with the anchoring wire, and an inflation lumen operatively attached to the at least one balloon. The delivery system can further comprise a guidewire that is slideably engageable with the anchoring wire delivery catheter and which can be used to position the anchoring wire delivery catheter in a desired location relative to the patient.

BRIEF DESCRIPTION OF THE DRAWINGS

The present invention will be further explained with reference to the appended Figures, wherein like structure is referred to by like numerals throughout the several views, and wherein:

FIG. 8a is a top view of the distal end portion of the centering introducer and balloon illustrated in FIG. 7;

FIG. 8b is a cross-sectional view of a portion of the centering introducer taken along section line 1-1 of FIG. 8a;

FIGS. 10 through 16 are partial sectional perspective views of a heart as a delivery system is being guided, navigated, and deployed into the area of the native mitral valve.

DETAILED DESCRIPTION

Figure 1:
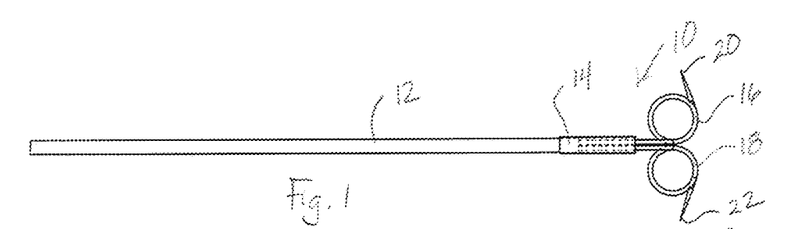
FIG. 1 is a front view of an anchoring wire assembly of an exemplary embodiment of a delivery system of the invention.
Figure 2:
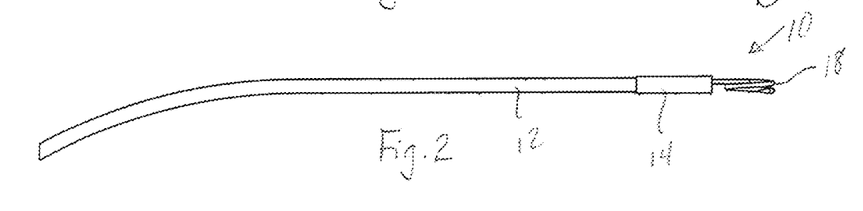
FIG. 2 is a top view of the anchoring wire assembly illustrated in FIG. 1.

Referring now to the Figures, wherein the components are labeled with like numerals throughout the several Figures, and initially to FIG. 1, one exemplary configuration of a distal end portion of an embodiment of an anchoring wire assembly 10 of the invention is illustrated. Anchoring wire assembly 10 generally includes an anchor wire 12 attached by a crimp sleeve 14 to two anchor loops 16, 18. The anchor loops 16, 18 may be fabricated of platinum, stainless steel, Nitinol, an alloy of the type commercially available under the trade designation MP35N, or other biocompatible metal. In one embodiment, the anchor loops 16, 18 are made of a shape memory material and formed into a loop or coil that that can be at least partially straightened or deformed by the application of a force, then can return generally to the loop or coil configuration when that force is removed or reduced. Each of the anchor loops 16, 18 includes its own respective distal tip 20, 22, which can be relatively sharp for penetration into the tissue of a patient, as will be described below.

The anchor loops 16, 18 can be crimped or otherwise attached to the anchor wire 12 via the crimp sleeve 14, which can be made of stainless steel, for example. The crimp sleeve 14 can initially be a generally tubular shaped portion that can optionally first be attached to the anchor wire 12 at its proximal end, such as by crimping, adhesives, or the like. The ends of the anchor loops 16, 18 that extend from the curved portion can then be inserted into the distal end of the crimp sleeve 14 by a desired amount, after which the crimp sleeve 14 can be compressed until it is sufficiently tight around the anchor wire 12 and anchor loops 16, 18 to securely attach the components to each other. Alternatively, the crimp sleeve 14 can be a separate component that is attached to the anchor wire 12 and anchor loops 16, 18 simultaneously, such as positioning a proximal end of the crimp sleeve over a distal end of the anchor wire 12, inserting the wires of the anchor loops 16, 18 into the proximal end of the anchor wire 12, then compressing the crimp sleeve 14 onto the anchor wire 12 and anchor loops 16, 18 with the use of a single crimping tool or other compression device(s).

In yet another alternative, the anchor loops 16, 18 are adhered within the crimp sleeve 14, which may or may not also need to be compressed to further secure the components to each other. In yet another alternative, the anchor loops 16, 18 are attached to the anchor wire 12 without the use of a crimp sleeve 14, such as by twisting the anchor loops onto the anchor wire 12 or by welding the anchor loops onto the end of the anchor wire 12, for example. In yet another alternative, the anchor loops 16, 18 are integrally formed with the anchor wire 12 so that the loops 16, 18 are extensions from the distal end of the anchor wire 12, rather than attachable components Like the anchor loops 16, 18, the anchor wire 12 may be fabricated of platinum, stainless steel, Nitinol, an alloy of the type commercially available under the trade designation MP35N, or other biocompatibie metal. In one embodiment, the anchor wire 12 is made of the same flexible wire material and assembly composition as that of a standard guidewire. The length of the wire 12 can vary, but is generally long enough to be able to extend outside the body of a patient when it is used for navigation into the patient and able to perform an exchange in accordance with the methods of the invention.

Figure 3:
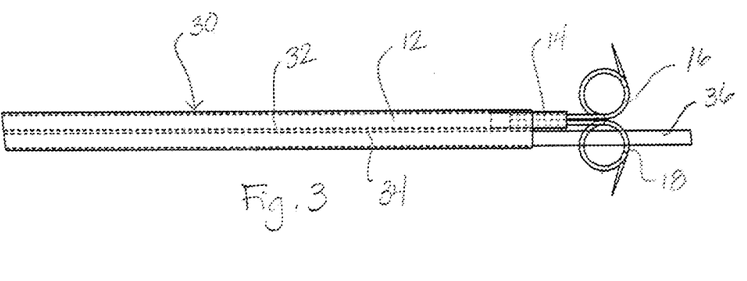
FIG. 3 is an enlarged front view of a distal end portion of a delivery system, which includes an anchoring wire assembly of the type illustrated in FIG. 1, along with an extending guidewire.
Figure 3B:
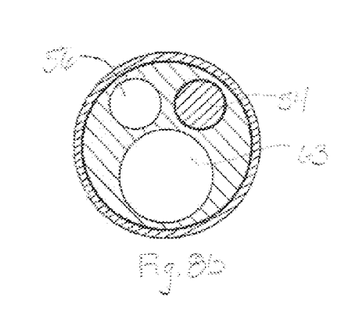
Figure 4:
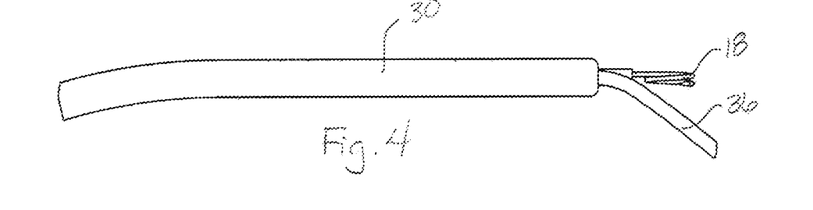
FIG. 4 is a top view of the distal end portion of the delivery system illustrated in FIG. 3.

The anchoring wire assembly 10 is insertable into one lumen of an anchoring wire assembly delivery system, which consists of a multi-lumen catheter, such as a lumen 32 of a dual-lumen catheter 30 that is illustrated in FIGS. 3 and 4. As shown, anchor wire 12 is enclosed within the lumen 32, with the anchor loops 16, 18 extending beyond a distal end of the catheter 30. If the assembly 10 includes a crimp sleeve 14, at least a portion of it can also extend beyond the distal end of the catheter 30 for full anchor deployment, or it can instead be enclosed within the lumen 32. The catheter 30 further includes a second lumen 34, in which a guidewire 36 is positioned. Guidewire 36 includes a distal end portion that extends beyond a distal end of the second lumen 34. The catheter 30 of this embodiment is preferably made of a flexible material that can track relatively easily along the length of the guidewire 36. It is understood that the catheter can further include one or more additional lumens for the insertion of other devices or components that can be used in accordance with the methods of the invention.

Figure 5:
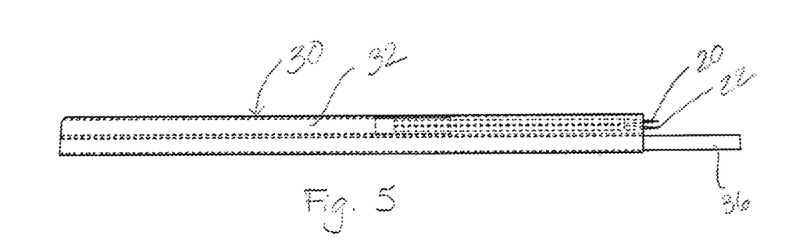
FIG. 5 is a front view of a distal end portion of a delivery system of the type illustrated in FIG. 3, which illustrates the anchoring wire assembly in a retracted position with its needle tips exposed.
Figure 6:
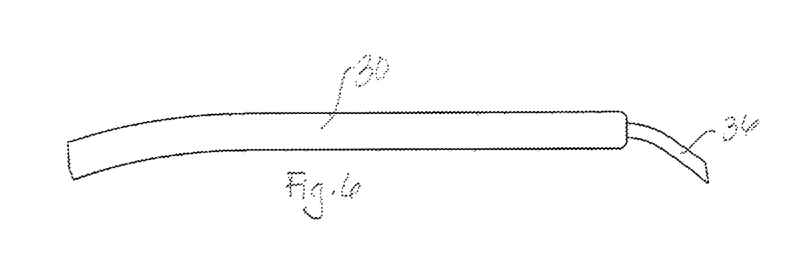
FIG. 6 is a top view of the distal end portion of the delivery system illustrated in FIG. 5.
Figure 6A:
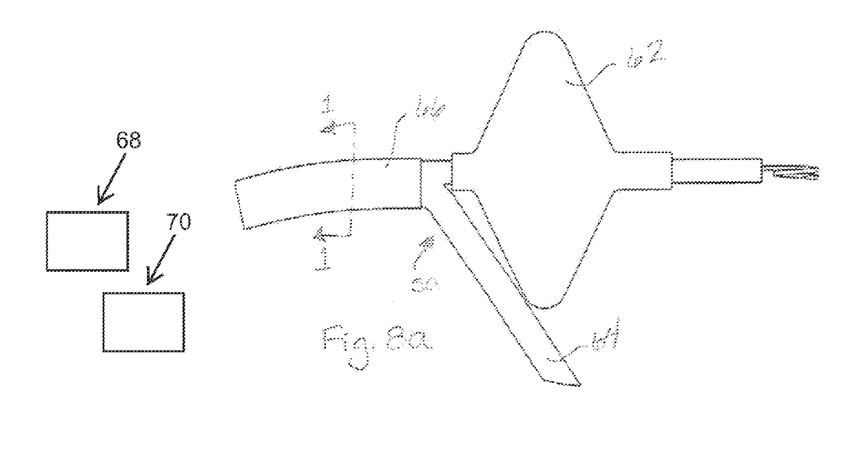

In order to prepare the catheter for insertion into a patient, the anchor wire 12 is pulled a proximal direction until the anchor loops 16, 18 are pressed against the distal end of the catheter 30. The anchor wire 12 is then pulled even further in the proximal direction until the wires of the anchor loops 16, 18 begin to come uncoiled and are pulled into the lumen 32. As shown in FIGS. 5 and 6, this movement of the anchor wire 12 relative to the distal end of catheter 30 can be continued until only the distal tips 20, 22 extend beyond the distal end of the catheter 30. In order to prevent interference between these distal tips 20, 22 and any tissue within the patient, these tips 20, 22 can be retracted even further into the lumen 32 so that they do not extend beyond the end of the catheter 30. The proximal end of the catheter 30 (not illustrated) can include a valve, such as a hemostasis valve, for both wires. A removable pin vise can be attached to the anchor wire 12 near the hemostasis valve to assist in the process of retracting the anchor wire 12 and its attached anchor loops 16, 18 and also in the deployment of these wires and loops.

Figure 7:
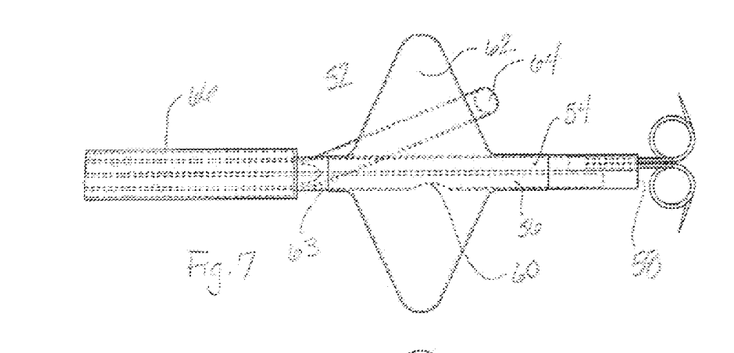
FIG. 7 is a front view of a distal end portion of a centering introducer and balloon in a deployed state.
Figure 17:
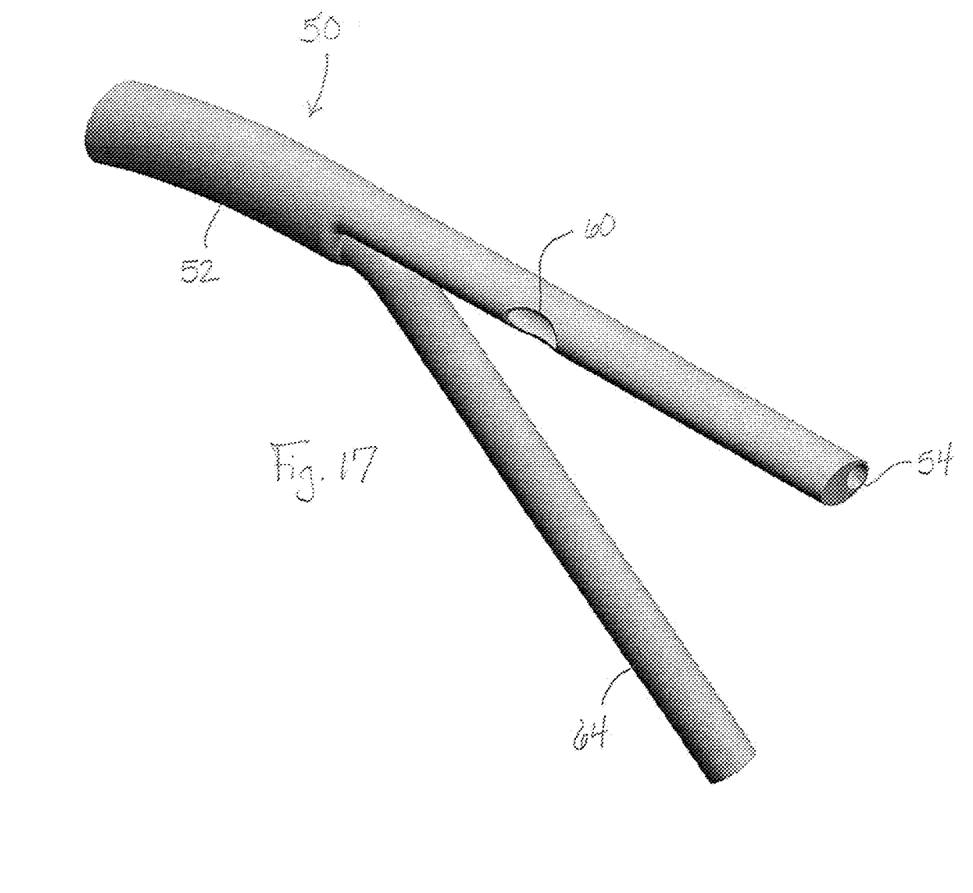
FIG. 17 is a perspective view of a centering introducer component of a delivery system in accordance with the invention.
Figure 18:
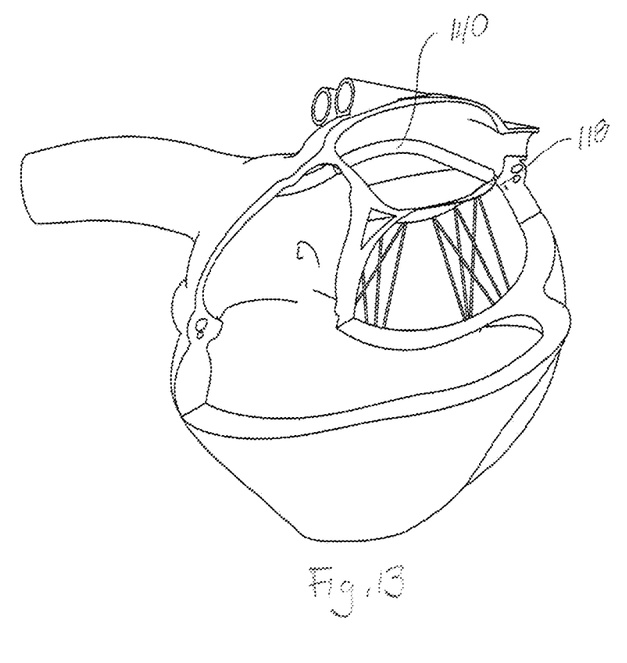

FIGS. 7, 8a, and 8b are front, top, and cross-sectional views, respectively, of an assembly that includes a centering introducer 50, and FIG. 17 is a perspective view of the centering introducer 50 separate from the other components of the assembly. Centering introducer generally includes a multi-lumen tube 52, such as a tri-lumen tube, which can be at least somewhat flexible along its length. It is contemplated that different portions of the tube 52 can have different flexibilities along its length. When used in accordance with methods of the invention that will be described in further detail below, the dual-lumen catheter 30 and guidewire 36 described above are removed from a patient to leave the anchor wire 12 secured within the patient, such that the multi-lumen tube 52 can then be guided along the anchoring wire 12 to position it in a desired location within a patient.

Centering introducer 50 includes a first lumen 54 of the tube 52 that extends along the tube length and which is positionable over the anchoring wire. Tube 52 also includes a second lumen 56 that extends along the tube length, but is plugged at its distal tip 58 and includes a notched area 60 that is open for communication with the inside of a balloon 62. Tube 52 further includes a third lumen 63 that extends through its length and then branches off from the main body of the centering introducer 50 adjacent to the balloon 62. This third lumen 63 may also be referred to as an introducer lumen, which can be used for helping to guide an end effector or introducer element 64 that extends from this lumen 63 and to a specific location, as will be described in further detail below.

The balloon 62 can be provided with a number of different shapes when it is expanded, such as the diamond-like shape illustrated in FIGS. 7 and 8, although it is understood that a number of different external shapes for the balloon can be used. When the device is inserted into a patient, the balloon will be unexpanded so that it is has a minimal profile size. However, after the device is located in a desired position within a patient, the balloon will be expanded in such a way that it will push the introducer element 64 away from the anchor wire 12. Thus, the size and shape of the balloon 62 can be designed or selected to provide a desired deflection of the introducer element when the balloon is inflated. The proximal end of the centering introducer (not illustrated) can include a handle that includes a valve (e.g., a small hemostasis valve) for the anchoring wire, a valve (e.g., a large hemostasis valve) for any device that is guided through the introducer lumen, and/or a port 68 for injection of saline or air into the lumen that is used to inflate the balloon.

The system may further include a separate flexible tube or sheath 66 that is positionable over the multi-lumen tube 52. The inside diameter of the sheath 66 is at least slightly larger than the outer diameter of the multi-lumen tube 52 so that it can move along the length of the tube 52. The sheath 66 can further be configured so that when it is moved toward the distal end of the delivery system, it can fully encase both the introducer element 64 and the balloon 62 (when the balloon is in its uninflated or semi-inflated condition).

Figure 9:
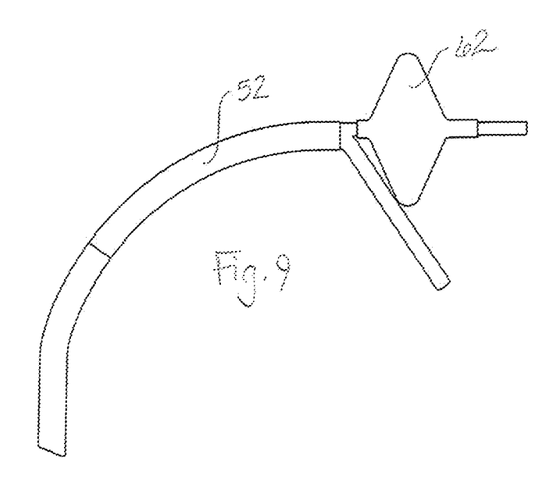
FIG. 9 is a top view of the distal end portion of the centering introducer and balloon illustrated in FIG. 8, and further illustrating a portion of the tubing that is adjacent to the distal end portion.

FIG. 9 illustrates an embodiment of the delivery system of the invention that includes a multi-lumen tube 52 that has a pre-set curve. The curve can provide the advantage of retaining the position of keeping the introducer element in a desired position relative to the balloon. The curve of this figure is only illustrative, and it is contemplated that the pre-set curve may have a larger or smaller radius than shown and/or the tube can include multiple sections that have different curves. For example, adjacent sections or lengths of the tube can have different radii of curvature in order to accommodate different patient anatomies. In addition, different curves can be attained with the use of a steerable catheter. It is further contemplated that the tubing can be at least slightly twisted along its length, such as to cause the introducer element to be able to track in a perpendicular direction to the distal tip when it is being inserted into a patient. In addition, it is contemplated that the tube can be sufficiently stiff so that it generally retains its shape when being inserted into a patient, but can also have enough flexibility so that it can be reconfigured prior to insertion of the delivery system into a patient, if desired.

Figure 10:
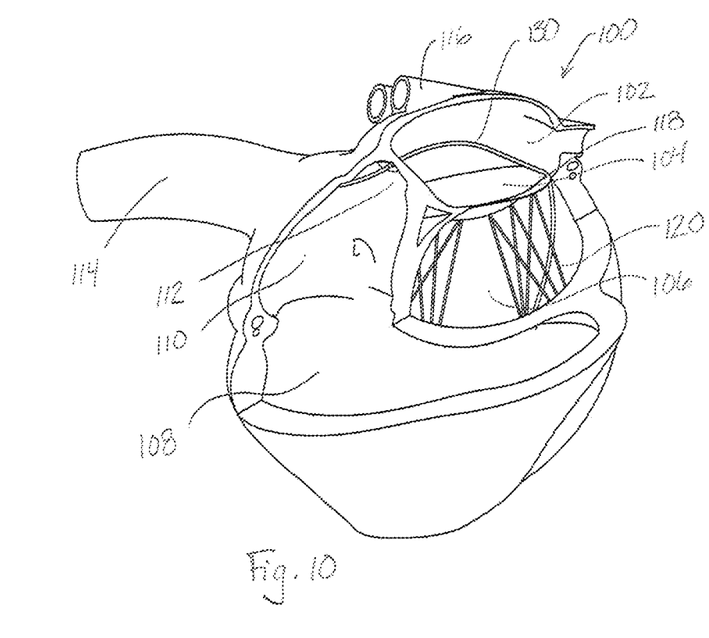

FIGS. 10 through 16 are partial sectional perspective views of a heart 100 with an embodiment of the delivery system of the invention as it can be guided, navigated, and deployed into the area of the native mitral valve. In particular, FIG. 10 illustrates a number of components of heart 100, including the left atrium 102, the mitral valve 104, the left ventricle 106, the right ventricle 108, the right atrium 110, the fossa ovalis 112, the inferior vena cava (IVC) 114, and the right pulmonary veins 116. The mitral valve 104 further includes an area that is commonly referred to as the A1-P1 commissure, which is generally designated with reference number 118. This nomenclature for the mitral valve is derived from its two primary leaflets, which are referred to as the anterior and posterior leaflets, each of which is further broken down into scallops or regions divided by commissures, or zones of apposition. Three regions are found on the anterior leaflet (A1 through A3) with opposing regions on the posterior leaflet (P1 through P3). The mitral valve 104 further includes multiple chordae 120 attaching to the anterior and posterior papillary muscles of the left ventricle 106.

A delivery system of the invention can be guided to the area of the mitral valve in a number of ways, one of which includes accessing the right atrium 110 through the femoral vein, while a trans-septal puncture would be used to gain access to the left atrium 102. A guidewire 130 can then be advanced into the left ventricle 106. In most cases, this guidewire 130 will naturally track into the A1-P1 commissure region 118, as is illustrated in FIG. 10. The stiffness of the guidewire 130 can be chosen or designed to provide for ease of tracking to the desired area, where a guidewire that is too flexible may have difficulty reaching the desired target area of the heart, such cases, it may be desirable to instead use a guidewire with a higher stiffness in order to increase the likelihood that the guidewire will more easily reach its desired location in the heart.

Figure 11:
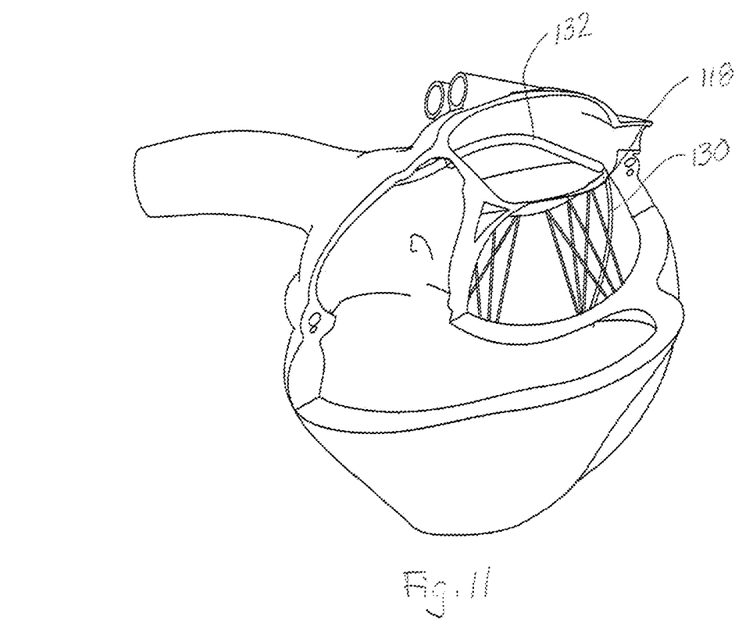
Figure 12:
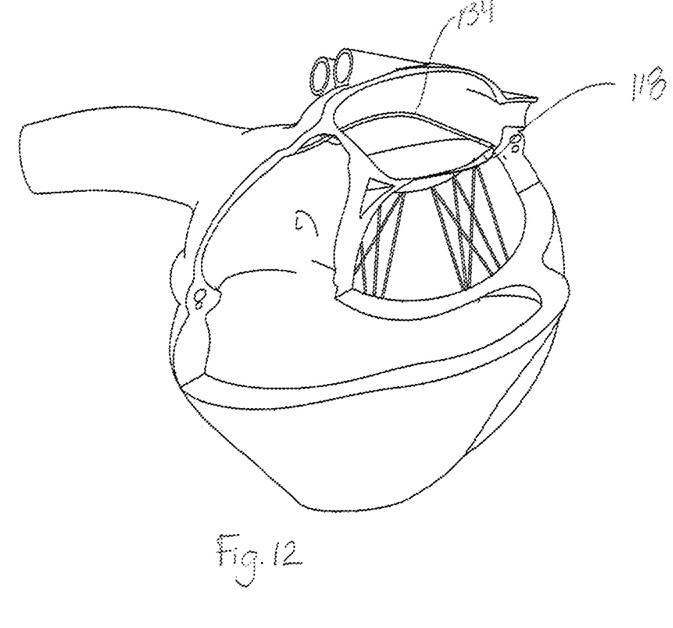

After the guide wire 130 is positioned in its desired location, a distal tip of an anchoring wire delivery catheter 132 can be guided forward over the guidewire 130 to the A1-P1 commissure region 118, as is illustrated in FIG. 11. The distal tip can be pressed against the annulus in the A1-P1 commissure region 118 as it is being monitored, such as can be accomplished using echo and/or tactile feedback. An anchor wire 134, which is located within the delivery catheter 132, can then be pushed forward to deploy the anchor into the annular tissue. In order to be sure the anchor is securely attached to the tissue, the user can pull the wire with slight to moderate tension in a direction that is opposite the deployment direction. Once the anchor wire is in place, the delivery catheter 132 can be removed, leaving only the anchor wire 134 in the patient, as is illustrated in FIG. 12.

Figure 14:
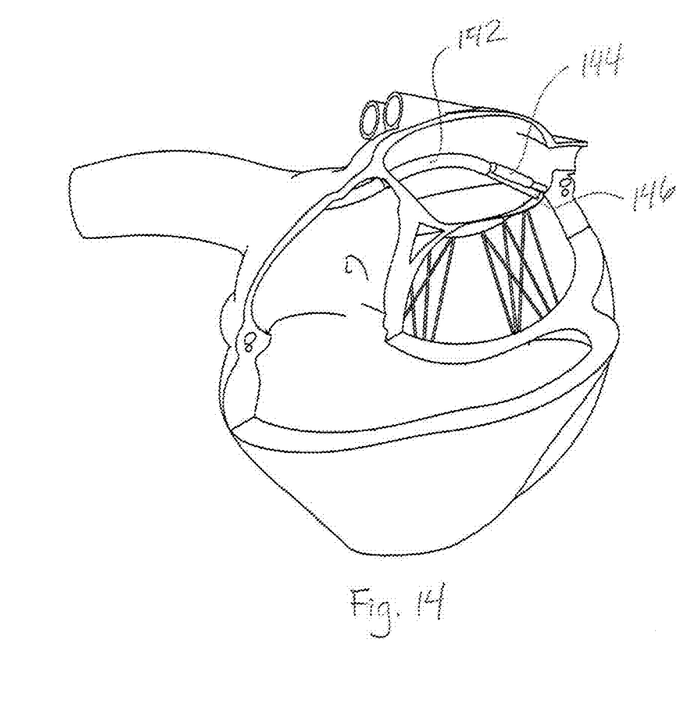

FIG. 13 illustrates a subsequent step in the delivery process, in which a centering introducer 140 is advanced over the anchor wire 134 and into the A1-P1 commissure region 118. At this point, a sheath 142 can be moved proximally to expose a balloon 144 and an introducer element 146 that can extend at an angle relative to the body of the delivery, system, as is illustrated in FIG. 14. Although a single balloon is illustrated in this embodiment, it is contemplated that the centering introducer may instead include multiple balloons, which may optionally each include their own inflation controls.

Figure 15:
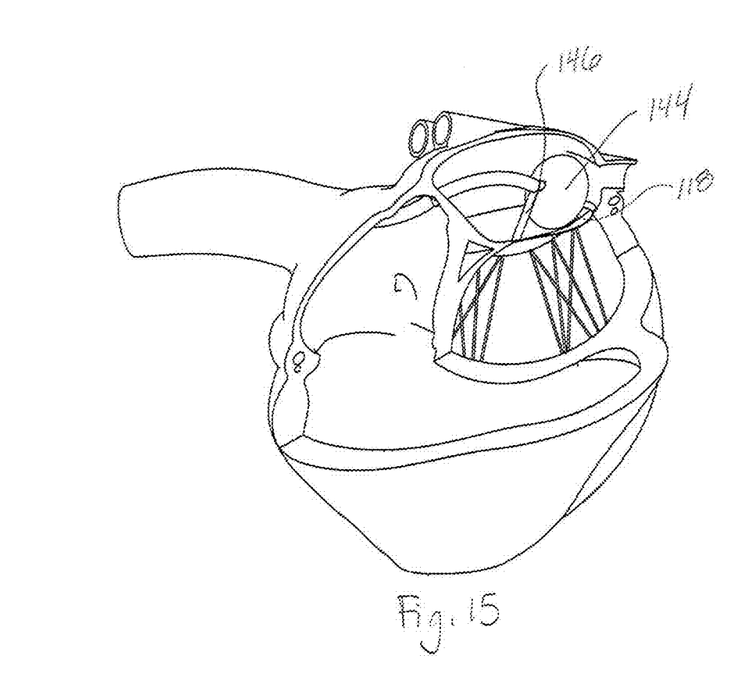

Referring now to FIG. 15, after the introducer element 146 and balloon 144 are in their desired locations in the patient, the balloon 144 can be inflated, which will contact and displace the introducer element 146. In one exemplary embodiment, inflation of the balloon 144 causes the introducer element 146 to travel across the mitral valve from the A1-P1 commissure region 118, where it was originally positioned, and toward another region of the native mitral valve (e.g., the A3-P3 commissure region). Displacement of the introducer element 146 can be controlled by monitoring and controlling the inflation of the balloon 144 and the corresponding amount of interference between the balloon 144 and the introducer element 146. Thus, different levels of balloon inflation will provide for access to different areas of the leaflets. In addition, the balloon can be designed and used in such a way the balloon 144 can also push off of the atrial wall, which can provide additional leverage for positioning the delivery system.

Figure 16:
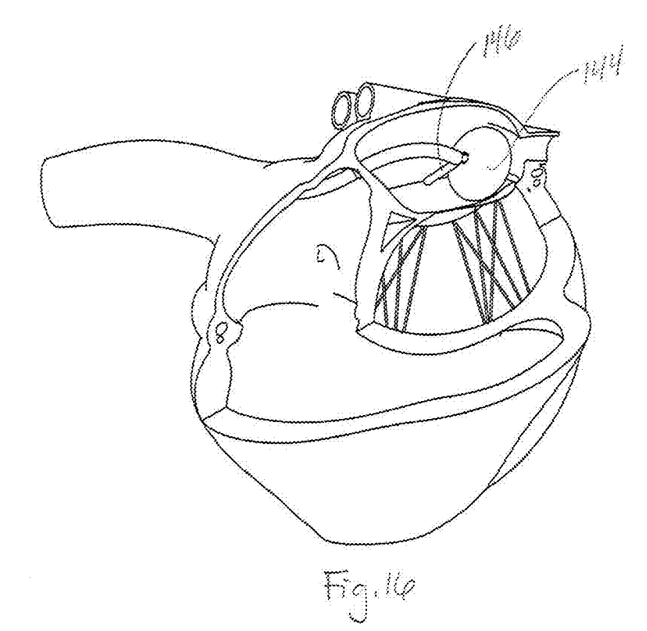

In cases where it is desired to obtain additional repositioning of the delivery system when it is in a patient, the proximal end or handle area of the delivery system can be rotated, as is illustrated in FIG. 16. Such a rotation of the system can allow the introducer element 146 to move across the valve and toward one of the annular regions. In order to achieve additional adjustability for the delivery system, tension can be applied to the anchor wire, and/or the entire catheter can be pushed or pulled, if desired.

After the centering introducer is positioned in its desired location relative to the native mitral valve, one or more procedures can be performed within the adjacent area of the heart. In such procedures, devices and instruments can be moved into the desired area of the heart via the introducer lumen and introducer element. For example, anchors can be inserted for a mitral valve annulus reduction or reshaping, a replacement mitral valve can be deployed and/or oriented, one or more clips can be inserted for mitral repair, and/or the like. For another example, the therapy delivery catheter can be inserted and advanced prior to navigation. In any case, when all of the desired procedures are completed, the delivery system can be removed from the patient. This may be accomplished by deflating the balloon, sliding the sheath toward the distal end of the delivery system to recapture the balloon and introducer element. In addition, the anchor wires can be pulled in a proximal direction until they are released from the mitral valve annulus area. The delivery system can then be removed from the heart of the patient.

The present invention has now been described with reference to several embodiments thereof. The entire disclosure of any patent or patent application identified herein is hereby incorporated by reference. The foregoing detailed description and examples have been given for clarity of understanding only. No unnecessary limitations are to be understood therefrom. It will be apparent to those skilled in the art that many changes can be made in the embodiments described without departing from the scope of the invention. Thus, the scope of the present invention should not be limited to the structures described herein, but only by the structures described by the language of the claims and the equivalents of those structures.

What is claimed is:

1. A method of positioning a centering introducer in a heart of a patient, comprising the steps of:
    inserting an anchoring wire delivery catheter through a heart wall and to a treatment region of the heart;
    deploying an anchoring wire from the anchoring wire delivery catheter and into tissue in the treatment region of the heart to anchor the anchoring wire, wherein a distal end of the anchoring wire pierces the tissue and is anchored in the tissue;
    removing the anchoring wire delivery catheter from the heart;
    advancing a centering introducer along the anchoring wire to the treatment region, wherein the centering introducer comprises an introducer element and at least one balloon separate from the introducer element;
    inflating the at least one balloon to contact an outer surface of the introducer element to reorient the introducer element in at least one direction relative to a longitudinal axis of the centering introducer and away from the anchoring wire.

2. The method of claim 1, wherein the step of inserting an anchoring wire delivery catheter further comprises inserting a guidewire through the heart wall and to the treatment region of the heart, and then advancing the anchoring wire delivery catheter along the guidewire.

3. The method of claim 1, wherein the treatment region of the heart comprises the annular region of a mitral valve.

4. The method of claim 1, further comprising the step of introducing a treatment device through the introducer element and into the treatment region of the heart.

5. The method of claim 4, wherein the treatment device comprises at least one of a clip, an anchor, and a replacement heart valve.

6. The method of claim 1, wherein at least a portion of the anchoring wire comprises a shape memory material.

7. The method of claim 6, wherein the step of deploying the anchoring wire comprises pressing a distal end of the anchoring wire delivery catheter against the tissue while the distal end of the anchoring wire is disposed within a lumen of the anchoring wire delivery catheter, and then pushing the anchoring wire distally out of the distal end of the anchoring wire delivery catheter so that the distal end of the anchoring wire extends from the anchoring wire delivery catheter to engage with the tissue in the treatment region.

8. The method of claim 1, wherein the centering introducer further comprises an anchoring wire lumen and an inflation lumen that is in communication with an interior area of the at least one balloon.

9. The method of claim 8, wherein the centering introducer further comprises a control device operatively connected to the anchoring wire and an injection port operatively connected to the at least one balloon.

10. The method of claim 1, wherein the centering introducer comprises multiple regions along its length, each of which comprises a different flexibility than at least one other region.

11. The method of claim 1, wherein the delivery system further comprises a sheath that is slideably positionable relative to the introducer element and balloon, and wherein the method further comprises sliding the sheath in a proximal direction to unsheath the introducer element and the at least one balloon.

12. The method of claim 11, further comprising a step of sliding the sheath in a distal direction to surround at least a portion of the introducer element and the at least one balloon prior to a step of removing the delivery system from the heart of the patient.

13. The method of claim 1, further comprising a step of rotating at least a portion of the centering introducer to move the introducer element to a desired location relative to the heart.

14. The method of claim 2, wherein the step of inserting an anchoring wire delivery catheter through a heart wall comprises moving the guidewire to the right atrium through a femoral vein, then moving the guidewire into the left atrium through a trans-septal puncture, and then moving the guidewire into the left atrium and to a commissure region of the mitral valve.

15. The method of claim 1, wherein the introducer element at least partially surrounds an introducer lumen, and wherein the at least one balloon does not surround the introducer lumen.

16. The method of claim 9, wherein the control device comprises a valve.

17. The method of claim 1, wherein the distal end of the anchoring wire is sharpened to pierce the tissue in the treatment region.

18. The method of claim 1, wherein the distal end of the anchoring wire includes an anchor loop that anchors the distal end of the anchoring wire in the tissue.

19. The method of claim 18, wherein the anchor loop is at least partially straightened and disposed within a lumen of the anchoring wire delivery catheter as the anchoring wire delivery catheter is advanced to the treatment region of the heart, and wherein the step of deploying the anchoring wire from the anchoring wire delivery catheter comprises pushing the anchoring wire out of a distal end of the lumen and into the tissue in the treatment region, wherein as the anchor loop is pushed out of the lumen the anchor loop regains its loop shape to anchor the distal end of the anchoring wire in the tissue.

* * * * *